(12) United States Patent
Fukushima et al.

(10) Patent No.: US 6,500,932 B1
(45) Date of Patent: Dec. 31, 2002

(54) ANTIHUMAN THYMIDYLATE SYNTHASE MONOCLONAL ANTIBODIES AND HYBRIDOMAS PRODUCING THE SAME

(75) Inventors: Masakazu Fukushima, Hanno (JP); Hiroyuki Okabe, Iruma (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/530,422

(22) PCT Filed: Aug. 31, 1999

(86) PCT No.: PCT/JP99/04710

§ 371 (c)(1),
(2), (4) Date: May 1, 2000

(87) PCT Pub. No.: WO00/12561

PCT Pub. Date: Mar. 9, 2000

(30) Foreign Application Priority Data

Sep. 1, 1998 (JP) ............................................ 10-247320

(51) Int. Cl.[7] .......................... C07K 16/00; C12N 5/06; C12N 5/16
(52) U.S. Cl. .................... 530/388.26; 435/331
(58) Field of Search ...................... 530/388.15; 435/331

(56) References Cited

FOREIGN PATENT DOCUMENTS

WO            92/19650      11/1992    ............ C07K/15/28

OTHER PUBLICATIONS

Proceedings of the American Association for Cancer Research 90th Annual Meeting, vol. 40, issued Mar. 1999, Okabe, H. et al., "Preparation and epitope analysis of monoclonal antibodies to recombinant human thymidylate synthase, and their application to clinical studies", #2647 (Copy submitted to USPTO by WIPO).

Database BIOSIS on Dialog, No. 199800321040, Behan, K.A. et al., "Epitope mapping of a series of human thymidylate synthase monoclonal antibodies", Cancer Research, vol. 58, No. 12, 2606–2611, Jun. 15, 1998 (Copy submitted to USPTO by WIPO).
Proceedings of the American Association for Cancer Research 88th Annual Meeting, vol. 38, issued Mar. 1997, Behan, K. et al., "Epitope mapping of a series of human thymidylate synthase monoclonal antibodies", (TS106, TS109 and TS110), #3180.
Cancer Research, vol. 51, No. 24, issued Dec. 15, 1991, Patrick G. Johnston et al., "Production and Characterization of Monoclonal Antibodies That Localize Human Thymidylate Synthase in the Cytoplasm of Human Cells and Tissue", pp. 6668–6676.
Biochemistry, vol. 24, No. 3, issued Jan. 29, 1985, Malgorzata M. Jastreboff et al., "Isolation and Functional Effects of Monoclonal Antibodies Binding to Thymidylate Synthase", pp. 587–592.
XP–002156191–Johnston, et al., "Immunological Quantitation of Thymidylate Synthase Using the Monoclonal Antibody TS106 in 5–Fluorouracii–Sensitive and–Resistant Human Cancer Cell Lines", Cancer Research, vol. 52, No. 16, Aug. 15, 1992.
International Search Report.

*Primary Examiner*—Anthony C. Caputa
*Assistant Examiner*—Natalie Davis
(74) *Attorney, Agent, or Firm*—Sughrue Mion, PLLC

(57) ABSTRACT

This invention relates to an anti-human thymidylate synthase monoclonal antibody capable of recognizing an epitope which exists in a region of 187th to 313th amino acids from an N-terminus in human thymidy late synthase, an anti-human thymidylate synthase monoclonal antibody capable of recognizing an epitope which exists in a region of from an N-terminus to a 61st amino acid in human thymidylate synthase, and also hybridomas capable of producing these monoclonal anti-bodies.

These monoclonal antibodies are useful for the immunological measurement of human thymidylate synthase.

5 Claims, 3 Drawing Sheets

ANTIHUMAN THYMIDYLATE SYNTHASE MONOCLONAL ANTIBODIES AND HYBRIDOMAS PRODUCING THE SAME

TECHNICAL FIELD

This invention relates to a novel monoclonal antibody to human thymidylate synthase and also to a hybridoma capable of producing the same.

BACKGROUND ART

Thymidylate synthase (EC2.1.1.45, hereinafter called "TS") is an enzyme that catalyzes a reaction in which thymidylic acid is formed from deoxyuridylic acid, plays a role to supply thymine which is a base specific to DNAs, and is one of principal rate-limiting enzymes for a DNA precursor supply pathway. Accordingly, its activity is known to become higher in thymi or tumor tissues where cell growth is active.

On the other hand, fluoropyrimidine antitumor drugs such as 5-fluorourasil and 5-fluorodeoxyuridine act against TS as a target enzyme, and for example, 5-fluorodeoxyuridine changes into fluorodeoxyuridylic acid in vivo and inhibits TS. In particular, fluoropyrimidine antitumor drugs are known to show high therapeutic effect and significant life prolongation for patients with a low level of TS expression in tumor cells but to exhibit low therapeutic effect for patients with TS in a high level ["Gan to Kagaku Ryoho (Cancers and Chemotherapy)", 24(6), 705–721 (1997)]. The measurement of TS is therefore important, for example, an advance measurement of the expression of TS in an excised tumor upon treatment for a cancer patient gives indications for the determination of a treatment method and for the selection of an antitumor drug.

An object of the present invention is therefore to provide an anti-human TS monoclonal antibody useful for the immunological measurement of human TS and also a hybridoma capable of producing the same.

DISCLOSURE OF THE INVENTION

With the foregoing circumstances in view, the present inventors have proceeded with various investigations. As a result, novel anti-human TS monoclonal antibodies have been obtained and moreover, these monoclonal antibodies have been confirmed to be useful for the immunological measurement of human TS, leading to the completion of the present invention.

The present invention therefore provides an anti-human TS monoclonal antibody capable of recognizing an epitope which exists in a region of 187th to 313th amino acids from an N-terminus in human TS, an anti-human TS monoclonal antibody capable of recognizing an epitope which exists in a region of from an N-terminus to a 61st amino acid in human TS, and also hybridomas capable of producing these monoclonal antibodies.

Incidentally, the recognition regions by the human TS monoclonal antibodies according to the present invention have been determined in accordance with the amino acid sequence of human TS described, for example, in Nucleic Acids Research, 13(6), 2035–2043 (1985) or the like.

BEST MODES FOR CARRYING OUT THE INVENTION

Figure 1:
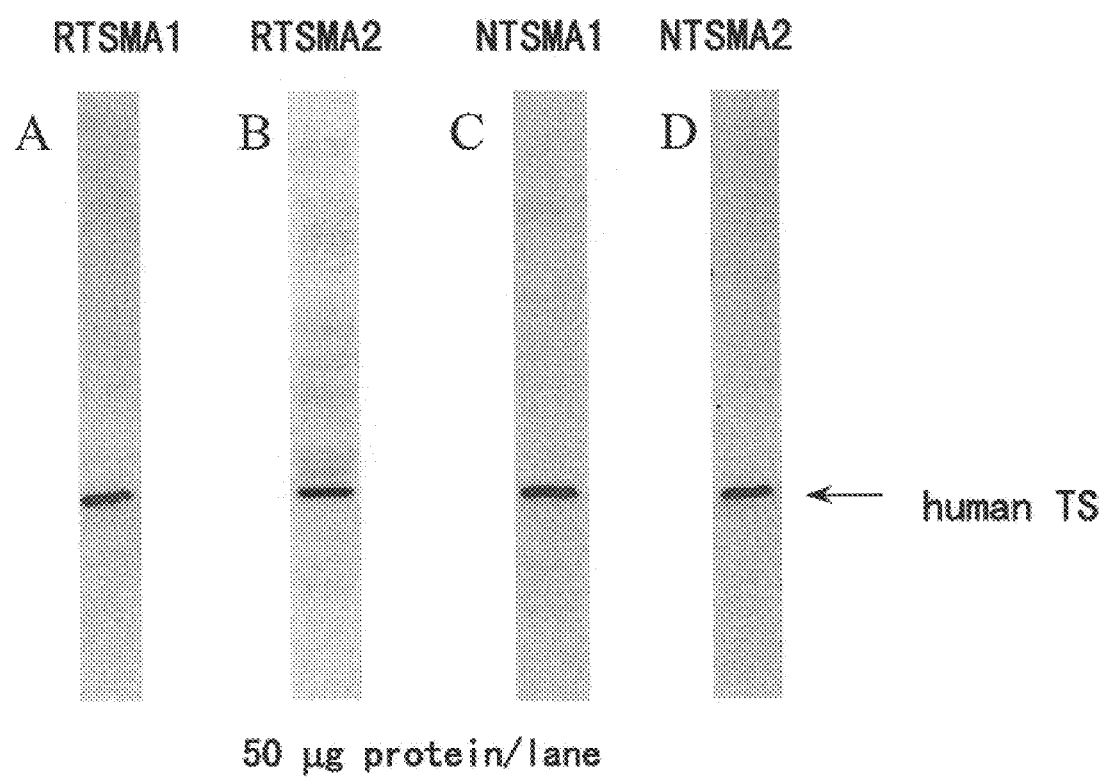
FIG. 1 electrophoretogrammatically shows recognition regions in TS by monoclonal antibodies according to the present invention.

Illustrative of the anti-human TS monoclonal antibody according to the present invention, which can recognize the epitope existing in the region of 187th to 313th amino acids from the N-terminus in human TS, are those produced by mouse hybridomas RTSMA1 (FERM BP-6404) and RTSMA2 (FERM BP-6402) obtained using, as an immunogen, a recombinant human TS (hereinafter called "rhTS") to be described subsequently herein. These hybridomas have been deposited under the Budapest Treaty in National Institute of Bioscience and Human-Technology, Agency of Industrial Science and Technology, Ministry of International Trade and Industry (address: 1–3, Higashi 1-chome, Tsukuba-shi, Ibaraki-ken 305–0046, JAPAN) (date of original deposit: Jun. 30, 1998).

The above rhTS can be produced as will be described hereinafter. Namely, a plasmid from which a glutathion S-transferase (GST)-TS fused protein can be derived by isopropyl-1-thio-β-D-galactoside (hereinafter called "IPTG") is prepared by inserting restriction enzyme recognition sites MunI to HindIII of cDNA of human TS into a plasmid designed to express the GST-TS fused protein. An *Escherichia coli* strain which has been transformed with the plasmid is mass-cultured in the presence of IPTG, and the crude GST-TS is loaded onto a glutathion-agarose column. The thus-adsorbed GST-TS fused protein is eluted with a suitable buffer, and is then incubated in the presence of thrombin and calcium chloride to cleave human TS and GST from each other. The resulting mixture is loaded further onto a GST-agarose column, whereby rhTS of high purity can be obtained.

On the other hand, examples of the anti-human TS monoclonal antibody of the present invention, which can recognize the epitope existing in the region of from the N-terminus to the 61st amino acid in human TS, can include those produced by mouse hybridomas NTSMA1 (FERM BP-6401) and NTSMA2 (FERM BP-6403) obtained using, as an immunogen, a native human TS (hereinafter called "nhTS") which is available from the tissues by extraction and purification. These hybridomas have been deposited under the Budapest Treaty in National Institute of Bioscience and Human-Technology, Agency of Industrial Science and Technology, Ministry of International Trade and Industry (address: 1–3, Higashi 1-chome, Tsukuba-shi, Ibaraki-ken 305–0046, JAPAN) (date of original deposit: Jun. 30, 1998).

The above nhTS can be produced based on the method proposed by Rode et al. [Rode et al., Biochemical Pharmacology 29, 723 (1980)] as will be described hereinafter. Namely, nhTS of high purity can be obtained by loading a homogenate of incubated cells of a human lung cancer strain Lu-99 or of a tumor, which has been excised from a nude mouse or nude rat with sub-cutaneously transplanted Lu-99, onto a column with ethyl 10-formyl-5,8-dideazafolate immobilized therein as a ligand and then eluting nhTS with a buffer containing dUMP.

Each of the hybridomas according to the present invention can be obtained by immunizing a mammal, such as a mouse or a rat, or a bird with the rhTS or nhTS, subjecting its spleen cells and myeloma cells of a mammal, such as a mouse or a rat, to cell fusion in accordance with the method originally outlined by Kohler and Milstein [see Nature, 256, 495 (1975)], and then culturing the fused cells in a selection medium. The hybridomas RTSMA1 and RTSMA2 are obtained when rhTS is used as an immunogen, while the hybridomas NTSMA1 and NTSMA2 are obtained when nhTS is used as an immunogen.

No particular limitation is imposed on an immunization method. Immunization can be achieved, for example, by dissolving rhTS or nhTS in phosphate buffer, physiological saline or the like, mixing an adjuvant as needed, and then administering the resulting solution several times at intervals of 1 to 3 weeks under the skin or into the spleen or peritoneal cavity or a vein of the animal. Illustrative of myeloma cells usable for cell fusion are mouse P3-NS-1/1Ag4.1, P3-X63-Ag8.653 and SP2/0Ag14 and rat YB2/0. Upon cell fusion, polyethylene glycol, Sendai virus or the like can be used as a fusion promoter, or electric pulses may be used.

The anti-human TS monoclonal antibodies according to the present invention can each be produced by culturing the corresponding one of the above-described hybridomas in a suitable culture medium or within the peritoneal cavity of a mammal (for example, mouse). An illustrative medium suitably usable for the incubation of the hybridoma is a media which contains bovine fetal serum, L-glutamine, L-pyruvic acid, and antibiotics (penicillin G and streptomycin) in Dulbeccos modified Eagle's minimum essential medium. The incubation of the hybridoma is conducted, for example, in a 5% $CO_2$ concentration at 37° C. for 3 days when it is performed in a culture medium or, for example, for 14 days when it is performed within the peritoneal cavity of a mouse. From the culture medium or mammalian ascites obtained as described above, the corresponding anti-human TS monoclonal antibody RTSMA1, RTSMA2, NTSMA1 or NTSMA2 according to the present invention can be separated and purified by a method commonly employed for the isolation and/or purification of proteins. Examples of such a method can include salting-out with ammonium sulfate, ion-exchange column chromatography making use of an ion-exchange cellulose, molecular sieve column chromatography making use of a molecular sieve gel, affinity column chromatography making use of polysaccharide complexed with protein A, dialysis, and lyophilization.

The anti-human TS monoclonal antibodies of the present invention obtained as described above are useful for the immunological measurement of human TS, and can be applied, for example, to the sandwich method, competitive radioimmunoassay, enzyme immunoassay and immunochromatography. When plural ones of the monoclonal antibodies according to the present invention are used in combination in these measuring methods, combinations of antibodies the epitopes of which are apart are preferred for obtaining high absorbances. It is therefore preferred to combine RTSMA1 or RTSMA2 with NTSMA1 or NTSMA2.

Further, a combination of an anti-human TS polyclonal antibody immobilized on an insoluble carrier makes it possible to easily measure human TS with high accuracy. Such an anti-human TS polyclonal antibody can be obtained in a manner known per se in the art by administering nhTS or rhTS to a suitable mammal such as mouse, rat, rabbit or sheep.

EXAMPLES

The following examples are presented to illustrate the present invention in further detail, but it is to be understood that the present invention is not limited thereto.

Referential Example 1

A. Preparation of rhTS

An *Escherichia coli* strain NM522, in which a plasmid prepared with restriction endonuclease recognition sites MunI to HindIII of human TS cDNA inserted therein to express a fused protein of glutathione S-transferase (GST) and human TS was incubated overnight at 37° C. under shaking in LB medium (200 mL) (product of Wako Pure Chemical Industries, Ltd.) in the presence of ampicillin (50 ug/mL). The culture medium was poured in 100 mL aliquots into two Erlenmeyer flasks which contained ampicillin-containing LB medium (1 liter/flask). They were incubated at 25° C. for 3 hours under shaking, to which 0.6 mL aliquots of isopropyl-1-thio-β-D-galactoside (IPTG, 40 mg/mL) were added respectively, followed by further incubation at 25° C. for 20 hours. cells were collected by centrifugation and were then suspended in a disrupting buffer (100 mL; 50 mM Tris, pH 7.5, 25% sucrose). "10% Nonidet P-40" (5 mL; sur- factant, product of NACALAI TESQUE INC.) and 1 M magnesium chloride (0.5 mL) were added. The cells were disrupted by a sonicator, followed by centrifugation at 10,000 rpm for 15 minutes. The supernatant was caused to pass (20 mL/hr) through a column packed with glutathione (GSH)-agarose (14 mL; product of Sigma Chemical Co.). After the column was washed with a wash (100 mL; 20 mM Tris, pH 7.5, 2 mM magnesium chloride, 1 mM DTT), the column was eluted with an eluent (50 mL; 50 mM Tris, pH 9.6, 5 mM GSH) such that the eluate was received in 3-mL aliquots in tubes. By confirming protein fractions in accordance with the Bradford's method, peak fractions (9 mL; protein concentration: 7 mg/mL) were obtained. They were immediately dialyzed against a wash (1 liter) to lower their pH back to 7.5, and thrombin (600 units) was added. The mixture so prepared was treated at 37° C. for 2 hours in the presence of 1 mM calcium chloride, whereby the GST-TS fused protein was cleaved at bound sites. The resulting mixture of GST and TS was again caused to pass through a GSH-agarose column (20 mL/hour), the column was eluted with a wash, and protein fractions were confirmed by the Bradford's method, whereby an rhTS solution (9 mL) was obtained. 0.2, 0.4, 0.6, 0.8 and 1.0 mg/mL BSA solutions (100 μL) were added to 5-mL aliquots of the Bradford's solution, respectively, and their absorbances at 595 nm were measured to prepare a standard curve. An rhTS solution (100 μL), which had been diluted fivefold in distilled water, was added to the Bradford's solution (5 mL) and the absorbance at 595 nm was measured. As a result, the protein concentration of the rhTS solution was found to be 3.5 mg/mL.

B. Preparation of nhTS

Purification of nhTS was conducted based on the method proposed by Rode et al. [Rode et al., Biochemical Pharmacology, 29, 723 (1980)]. A human lung cancer strain Lu-99, which had been subcutaneously transplanted to dorsal regions of 50 male BALB/c-nu/nu mice, was removed to obtain tumors (50 g). Those tumors were added with 10 mM phosphate buffer (100 mL; pH 7.5, 100 mM potassium chloride, 10 mM 2-mercaptoethanol) and were then homogenized. The homogenate was centrifuged at 4° C. and 10,000 rpm for 1 hour, and from the supernatant, a precipitate was obtained with ammonium sulfate at 30–70% saturation. The precipitate was dissolved in 10 mM phosphate buffer (pH 7.5, 0.1% Triton X-100, 10 mM 2-mercaptoethanol, 20 μM dUMP). The resulting solution was loaded onto a column while using ethyl 10-formyl-5,8-dideazafolate as a ligand. After the column was washed with 200 mM phosphate buffer (pH 7.5, 0.1% Triton X-100, 10 mM 2-mercaptoethanol, 20 μM dUMP), the column was eluted with 200 mM phosphate buffer (pH 7.5, 0.1% Triton X-100, 10 mM 2-mercaptoethanol, 20 µM dUMP) and an nhTS solution (4 mL) was obtained. 0.2, 0.4, 0.6, 0.8 and 1.0 mg/mL BSA solutions (100 µL) were added to 5-mL aliquots of the Bradford's solution, respectively, and their absorbances at 595 nm were measured to prepare a standard curve. An nhTS solution (100 µL) was added to the Bradford's solution (5 mL) and the absorbance at 595 nm was measured. As a result, the protein concentration of the nhTS solution was found to be 0.3 mg/mL.

Example 1
Preparation of Monoclonal Antibodies RTSMA1 and RTSMA2

To a female BALB/c mouse (8 weeks old), the rhTS obtained in Referential Example 1A was intraperitoneally injected at a dose of 20 µg/mouse. The TS protein was used in a form emulsified beforehand in Freund's complete adjuvant. To the mouse, the rhTS in a form emulsified beforehand in Freund's incomplete adjuvant was additionally and intraperitoneally injected at a dose of 20 µg/mouse four times successively at intervals of 14 days. Three days before fusion, the rhTS (100 µg) in phosphate-buffered physiological saline (0.5 mL) was injected through a caudal vein. Spleen cells ($1 \times 10^8$) from the immunized mouse, P3-X63- Ag8.653 myeloma cells ($2 \times 10^7$) and as a fusing reagent, "50% (V/V) polyethylene glycol 4000" (product of Merck & Co., Inc.) were used to fuse those cells together in accordance with the fusing method proposed by Galfre and Milstein [Galfre et al., Nature 266, 550 (1977)].

After the fusion, cells were suspended in HAT medium (RPMI1640 medium containing $1 \times 10^{-4}$ M hypoxanthine, $4 \times 10^{-7}$ M aminopterin and $1.6 \times 10^{-5}$ M thymidine), which contained 10% bovine fetal serum, to give a cell concentration of $1 \times 10^6$ cells/mL. The resultant suspension was dispensed in 200 µL aliquot per well onto a 96-well microplate. Fused cells were cultured in a $CO_2$ incubator (5% $CO_2$, 37°C.), during which replacements of the medium were conducted using HAT medium containing 10% bovine fetal serum so that the fused cells were allowed to proliferate. A hybridoma formed of the spleen cells and the myeloma cells were screened, and was then conditioned in HT medium (RPMI1640 medium containing $1 \times 10^{-4}$ M hypoxanthine and $1.6 \times 10^{-5}$ M thymidine) which contained 10% bovine fetal serum.

The antibody in the incubation supernatant of the hybridoma was detected in accordance with ELISA by using an rhTS-sensitized microplate. With respect to each well which was found to be positive, cloning was repeated twice in accordance with the limiting dilution analysis by using HT medium which containing 10% bovine fetal serum and 5% Bleiclone (product of Dainippon Pharmaceutical Co., Ltd.). Two kinds of clones which had reactivity to the rhTS were hence chosen, and were named "RTSMA1" (FERM BP-6404) and "RTSMA2" (FERM BP-6402).

Pristane (0.5 mL; product of Dainippon Pharmaceutical Co., Ltd.) was intraperitoneally injected to a nude mouse. Seven days later, pristane (0.5 mL) was intraperitoneally administered further, and the hybridomas RTSMA1 and RTSMA2 ($1 \times 10^7$ cells) were transplanted to the peritoneal cavity and were allowed to proliferate. After 2 to 3 weeks, ascites was obtained. The ascites was caused to pass through a "Protein G Sepharose 4FF " column (product of Pharmacia AB). After the column was washed with a wash (20 mM sodium phosphate, pH 7.0), the monoclonal antibodies RTSMA1 and RTSMA2 produced by the respective clones were eluted with the eluent (0.1 M glycine, pH 2.7) and were immediately dialyzed against a wash.

Example 2
Preparation of Monoclonal Antibodies NTSMA1 and NTSMA2

In a similar manner as in Example 1 except that as an immunogen, the nhTS obtained in Referential Example B1 was used in place of the rhTS, two kinds of clones having reactivity to the nhTS were chosen, and were named "NTSMA1" (FERM BP-6401) and "NTSMA2" (FERM BP-6403). From these hybridomas, monoclonal antibodies NTSMA1 and NTSMA2 were then obtained in a similar manner as in Example 1.

Test 1 Identification of Recognition Sites by the Monoclonal Antibodies According to the Present Invention Separately transformed in the *Escherichia coli* strain NM522 were plasmids which had been prepared to express GST-human TS fused proteins by inserting the restriction endonuclease recognition sites MunI to SphI (which encode the amino acids of human TS from the N-terminus to the 61st amino acid), the restriction endonuclease recognition sites MunI to BglII (which encode the amino acids of TS from the N-terminus to the 186th amino acid) and the restriction endonuclease recognition sites MunI to HindIII (which encode the amino acids of TS from the N-terminus to the 313th amino acid), respectively. The respective *Escherichia coli* clones were incubated overnight at 37° C. under shaking in LB medium (5 mL) (product of Wako Pure Chemical Industries, Ltd.) in the presence of ampicillin (50 µg/mL) and 1 mM IPTG.

The culture medium was transferred in 100 µL aliquots into 1.5 mL centrifuge tubes. Subsequent to centrifugation at 12,000 r.p.m. for 5 minutes, the supernatants were discarded. An electrophoresis sample preparation solution (100 µL) (4% SDS, 10% β-mercaptoethanol, 20% glycerol, 125 mM Tris-, pH 6.8) was added the resulting pellets to suspend them. The suspension was heated for 15 minutes on boiling water, and a 10-µL aliquot was then used for electrophoresis. After the sample was allowed to migrate using 12.5% polyacrylamide gel, the sample so migrated was electrically transferred onto a PVDF filter. The PVDF filter was then immersed in "BLOCK ACE" (blocking agent, product of Dainippon Pharmaceutical Co., Ltd.) to conduct blocking.

Using as primary antibodies the respective monoclonal antibodies prepared to 5 µg/mL with 20 mM PBS (pH 7.0), reactions were conducted for 1 hour. After the filter was washed with 20 mM Tris pH 7.0 (wash) which contained 500 mM sodium chloride and 0.05% Tween 20, reactions were conducted for 1 hour by using a biotinylated goat anti-mouse IgG antibody (product of VECTASTAIN) as a secondary antibody. The filter was then washed with a wash, and "ABC Reagent" (alkaline-phosphatase-labeled avidin-biotin complex solution, product of VECTASTAIN) was reacted. After washing with a wash, enzyme reactions were conducted by using an "Alkaline Phosphatase Substrate KIT II" (product of VECTASTAIN) to detect TS.

As a result, as is shown in FIG. 1, the monoclonal antibodies RTSMA1 and RTSMA2 recognized the TS protein over the entire length thereof, but did not recognize the reconstructed TS protein ranging from the N-terminus to the 186th amino acid. The antigen recognition sites (epitopes) of both of the antibodies were therefore found to exist in the region of from the 187th to 313th amino acids. On the other hand, the monoclonal antibodies NTSMA1 and NTSMA2 recognized all of the region ranging from the N-terminus to the 61st amino acid, the region ranging from the N-terminus to the 186th amino acid, and the reconstructed TS protein over the entire length thereof. The epitopes of these antibodies were hence found to exist in the region of from the 1st to 61st amino acids.

Test 2 Confirmation of Specificity of Monoclonal Antibodies of the Present Invention by Western blotting A cell homogenate of human leukemia derived cell CCRF-CEM (protein concentration: 10 mg/mL) was mixed with an equiamount of an electrophoresis sample preparation solution (4% SFS, 10% β-mercaptoethanol, 20% glycerol, 125 mM Tris, pH 6.8). The mixture was heated for 2 minutes in boiling water, and a 10-μL aliquot was then used for electrophoresis. After the sample was allowed to migrate using 12.5% polyacrylamide gel, the sample so migrated was electrically transferred onto a PVDF filter. The PVDF filter was then immersed in "BLOCK ACE" (blocking agent, product of Dainippon Pharmaceutical Co., Ltd.) to conduct blocking.

Using as primary antibodies the respective monoclonal antibodies prepared to 5 μg/mL with 20 mM PBS (pH 7.0), reactions were conducted for 1 hour. After the filter was washed with 20 mM Tris pH 7.0 (wash) which contained 500 mM sodium chloride and 0.05% Tween 20, reactions were conducted for 1 hour by using a biotinylated goat anti-mouse IgG antibody (product of VECTASTAIN) as a secondary antibody. The filter was then washed with a wash, and "ABC Reagent" (product of VECTASTAIN) was reacted. After washing with a wash, enzyme reactions were conducted by using an "Alkaline Phosphatase Substrate KIT II" (product of VECTASTAIN) to detect TS.

Figure 2:
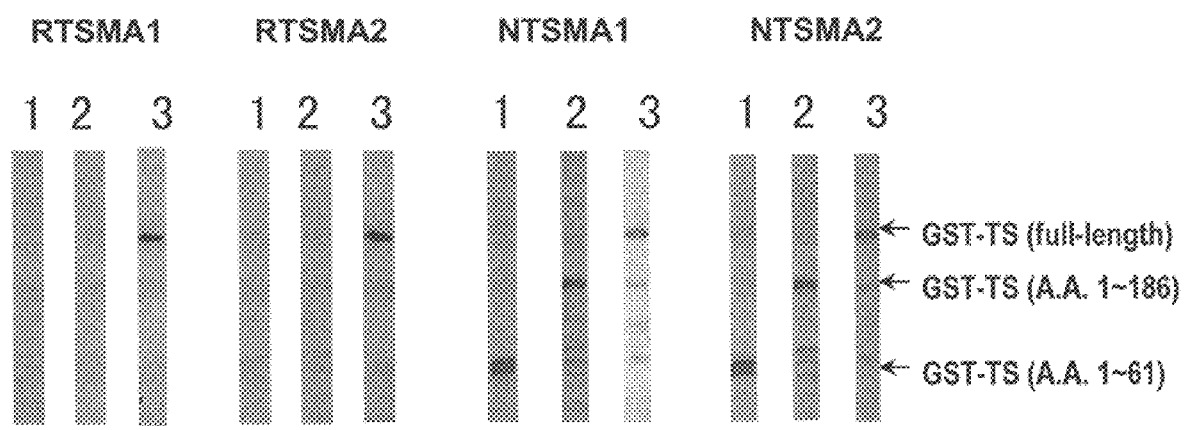
FIG. 2 electrophoretogrammatically illustrates detection results of human TS by Western blotting in which the monoclonal antibodies according to the present invention were used.

As a result, as is shown in FIG. 2, the monoclonal antibodies according to the present invention were all confirmed to specifically recognize only TS.

Test 3 Reactivity of the Monoclonal Antibody of the Present Invention to rhTS An rhTS solution, which had been adjusted to 10 μg/mL with 50 mM carbonate buffer (pH 9.5), was poured in 0.1 mL aliquots into the respective wells of a 96-well plate ("Immunoplate II Maxisope", product of Nunc). While keeping the plate sealed, coating was conducted for 1 hour to immobilize the antibody. The 96-well plate was washed twice with a wash (physiological saline containing 0.05% Tween 20), "BLOCK ACE" (blocking solution, product of Dainippon Pharmaceutical Co., Ltd.) was poured in 200 μL aliquots into the respective wells, and blocking was then performed for 1 hour at sites where the antibody was non-specifically adsorbed.

The blocking solution was then discarded, and as primary antibodies, the respective monoclonal anti-bodies (0.1 mL) which had been adjusted to 0.00244 to 5 μg/mL by diluting 5 μg/mL, as an initial concentration of dilution, twofold in 20 mM PBS (pH 7.0) were added and then reacted for 1 hour. The resulting mixture was washed twice with a wash, and the biotinylated goat anti-mouse IgG antibody (100 μL) (product of VECTASTAIN) was added, followed by reactions for 1 hour as in the case of the primary antibodies. After completion of the reactions, the reaction mixture was washed twice with a wash. The ABC reagent (100 μL) (product of VECTASTAIN) was added, and subsequent to completion of reactions for 1 hour, the reaction mixture was washed four times with a wash. A diethanolamine buffer (0.1 mL) (product of Kirkegaard and Perry Laboratories which contained 1 mg/mL paranitrophenylphosphate was added, followed by enzyme reactions for 10 minutes. 0.1 mL aliquots of 0.1 M sodium hydroxide were added to terminate the reactions, and measurements were conducted with the measuring absorbance of an ELISA plate reader set at 405 nm.

Figure 3:
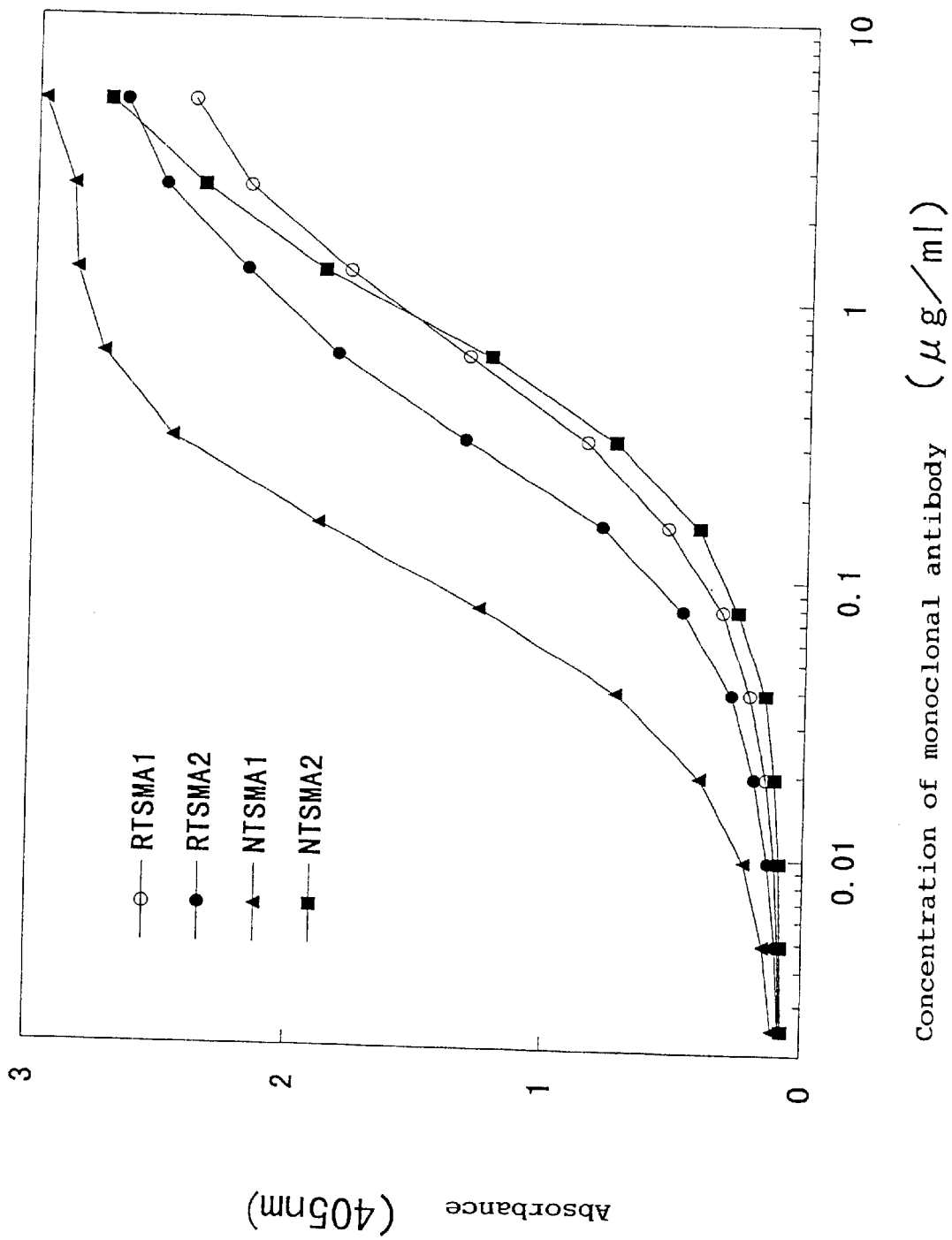
FIG. 3 diagrammatically depicts measurement results of human TS by ELISA in which the monoclonal antibodies according to the present invention were used.

As a result, as is shown in FIG. 3, the monoclonal antibodies RTSMA1, RTSMA2, NTSMAL and NTSMA2 gave absorbances of 0.3 or higher (background: 0.08) when used at concentrations of 0.08, 0.08, 0.02 and 0.16 μg/mL, respectively, and were able to achieve detection of rhTS at these concentrations.

Test 4 Comparison of Antibody Combinations by the Sandwich Method

The monoclonal antibodies RTSMA1 and RTSMA2 were adjusted to 2 μg/mL with 50 mM carbonate buffer (pH 9.5) and then dispensed in 0.1 mL aliquots onto a 96-well ELISA plate. The plate was sealed and was then subjected to coating for 2 hours in an incubator controlled at 37° C., whereby an antibody-immobilized carrier was obtained. After the carrier was washed twice with a wash (physiological saline containing 0.05% Tween 20), rhTS which had been adjusted to 10 μg/mL with 20 mM PBS (diluting solution) containing 0.05% Tween 20 was dispensed in 0.1 mL aliquots onto the antibody-immobilized plate and was then statically reacted at 37° C. for 1 hour.

After the wells were washed twice with a wash, the enzyme-labeled products of the monoclonal antibodies bodies RTSMA1, RTSMA2, NTSMAl and NTSM2 which had been adjusted to 1 μg/mL with the diluting solution were dispensed in 0.1 mL aliquots, and were statically reacted at 37° C. for 1 hour. After the wells were washed four times with a wash, 0.1 mL aliquots of 0.1 M acetate buffer (pH 5.5; color-developing solution) which contained 3 mg/mL orthophenylenediamine and 0.75 mM hydrogen peroxide were added, and enzyme reactions were allowed to proceed at room temperature for 30 minutes in a dark place. Finally, 0.1 mL aliquots of 0.1 M sulfuric acid were added to terminate the reactions, and measurements were conducted with the measuring absorbance of an ELISA plate reader set at 490 nm. The results are presented in Table 1.

TABLE 1

| | Differences in Absorbance (490 nm) by Combinations of Antibodies | | | |
|---|---|---|---|---|
| | Enzyme-labeled antibody | | | |
| Immobilized antibody | RTSMA1 | RTSMA2 | NTSMA1 | NTSMA2 |
| RTSMA1 | 0.4 | 0.4 | 7.2 | 4.0 |
| RTSMA2 | 0.8 | 0.4 | 8.0 | 4.2 |

As is apparent from Table 1, absorbance is low when monoclonal antibodies the epitopes of which are close to each other are used as an immobilized antibody and an enzyme-labeled antibody, but a high absorbance is available when monoclonal antibodies the epitopes of which are apart from each other are combined. The combination of anti-TS monoclonal antibodies the epitopes of which are apart from each other has made it possible to detect TS by the sandwich method.

Capability of Exploitation in Industry

As has been described above, the anti-human TS monoclonal antibodies according to the present invention are useful for the immunological measurement of human TS. Quantitation of human TS in a sample (for example, a stomach tissue extract) by their use permits not only determination of the presence or absence of a tumor, confirmation of therapeutic effect, and the like but also provision of an indication as to which treatment method should be chosen and whether or not administration of an antitumor drug is permissible.

What is claimed is:

1. An anti-human thymidylate synthase monoclonal antibody capable of recognizing an epitope within a region from the $267^{th}$ to the $282^{nd}$ amino acid from an N-terminus in human thymidylate synthase.

2. An anti-human thymidylate synthase monoclonal antibody capable of recognizing an epitope from the $267^{th}$ to the $282^{nd}$ amino acid from an N-terminus in human thymidylate synthase, which is produced by mouse hybridoma RTSMA1 (FERM BP-6404) or RTSMA2 (FERM BP-6402).

3. A hybridoma capable of producing an anti-human thyvidylate synthase monoclonal antibody, wherein said antibody is capable of recognizing an epitope within a region from the $267^{th}$ to the $282^{nd}$ amino acid from an N-terminus in human thymidylate synthase.

4. A hybridoma capable of producing an anti-human thymidylate synthase monoclonal antibody, wherein said hybridoma is mouse hybridoma RTSMA1 (FERM BP-6404) or RTSMA2 (FERM BP-6402).

5. An anti-human thymidylate synthase monoclonal antibody capable of recognizing an epitope that is recognized by a monoclonal antibody that is produced by mouse hybridoma RTSMA1 (FERM BP-6404) or RTSMA2 (FERM BP-6402).

\* \* \* \* \*

UNITED STATES PATENT AND TRADEMARK OFFICE
CERTIFICATE OF CORRECTION

PATENT NO.  : 6,500,932 B1
DATED       : December 31, 2002
INVENTOR(S) : Masakazu Fukushima and Hiroyuki Okabe It is certified that error appears in the above-identified patent and that said Letters Patent is hereby corrected as shown below:

Column 9,
Line 7, delete "thyvidylate" and insert -- thymidylate --.

Signed and Sealed this

Twenty-second Day of April, 2003

JAMES E. ROGAN
*Director of the United States Patent and Trademark Office*